US011524976B2

(12) United States Patent
Slavazza et al.

(10) Patent No.: US 11,524,976 B2
(45) Date of Patent: Dec. 13, 2022

(54) OLIGONUCLEOTIDE SYNTHESIZER

(71) Applicant: C S Bio Co., Menlo Park, CA (US)

(72) Inventors: Dario Slavazza, Menlo Park, CA (US); Heng Wei Chang, Menlo Park, CA (US); Yoheng Hanson Chang, Menlo Park, CA (US)

(73) Assignee: C S Bio Co., Menlo Park, CA (US)

( * ) Notice: Subject to any disclaimer, the term of this patent is extended or adjusted under 35 U.S.C. 154(b) by 0 days.

(21) Appl. No.: 17/005,854

(22) Filed: Aug. 28, 2020

(65) Prior Publication Data

US 2021/0061844 A1 Mar. 4, 2021

Related U.S. Application Data

(60) Provisional application No. 62/894,241, filed on Aug. 30, 2019.

(51) Int. Cl.
| | |
|---|---|
| *B01F 29/20* | (2022.01) |
| *B01F 35/53* | (2022.01) |
| *B01J 19/28* | (2006.01) |
| *B01F 29/60* | (2022.01) |
| *B01F 35/52* | (2022.01) |
| *C07H 21/00* | (2006.01) |
| *C07H 1/00* | (2006.01) |

(52) U.S. Cl.
CPC ............ *C07H 21/00* (2013.01); *B01F 29/20* (2022.01); *B01F 29/60* (2022.01); *B01F 35/52* (2022.01); *B01F 35/53* (2022.01); *B01J 19/28* (2013.01); *C07H 1/00* (2013.01); *B01J 2219/00722* (2013.01)

(58) Field of Classification Search
CPC .................................. C07H 21/00; C07H 1/00
See application file for complete search history.

(56) References Cited

U.S. PATENT DOCUMENTS

| | | | | | |
|---|---|---|---|---|---|
| 4,458,066 | A | * | 7/1984 | Caruthers | ............ B01J 19/0046 536/25.34 |
| 4,500,707 | A | * | 2/1985 | Caruthers | ............ B01J 19/0046 536/25.34 |
| 4,973,679 | A | * | 11/1990 | Caruthers | .............. C07H 21/00 536/25.3 |
| 5,132,418 | A | * | 7/1992 | Caruthers | ............ B01J 19/0046 536/25.3 |

(Continued)

FOREIGN PATENT DOCUMENTS

JP 2008-074979 * 4/2008 ............ C08F 212/36

OTHER PUBLICATIONS

Amarnath et al., "Chemical Reviews," 77(2), 183-217 (1977); see p. 209 at col. 1; "Synthesis on a Polymer Support."*

(Continued)

*Primary Examiner* — Eric Olson
(74) *Attorney, Agent, or Firm* — Morgan, Lewis & Bockius LLP

(57) ABSTRACT

A process for making an oligonucleotide, the process including reacting a oligonucleotide precursor with a solid phase support within a reaction vessel, the reaction vessel being coupled to an actuator and having a resting position and inverting the reaction vessel via the actuator such that the reaction vessel is inverted relative to the resting position, wherein the inversion of the reaction vessel results in stirring of the solid phase support within the reaction vessel.

16 Claims, 16 Drawing Sheets

(56) References Cited

U.S. PATENT DOCUMENTS

| | | | | |
|---|---|---|---|---|
| 5,153,319 A | * | 10/1992 | Caruthers | A61K 47/52 536/25.3 |
| 5,380,495 A | * | 1/1995 | Chang | B01J 19/0046 422/131 |
| 5,453,487 A | * | 9/1995 | Chang | B01J 19/0046 530/334 |
| 6,320,025 B1 | * | 11/2001 | Slavazza | B01J 19/0046 422/130 |
| 2003/0040011 A1 | * | 2/2003 | Barth | G01N 35/028 435/7.1 |

OTHER PUBLICATIONS

English machine translation of JP2008-074979, available from worldwide.espacened.com (Year: 2008).*

Wright et al., "Large Scale Synthesis of Oligonucleotides via Phosphoramidite Nucleosides and a High-loaded Polystyrene Support" Tetrahedron Letters vol. 34 No. 21 pp. 3373-3376 (Year: 1993).*

Gorman et al., "An Apparatus for Simultaneous Manual Solid-Phase Synthesis of Multiple Peptide Analogs" Analytical Biochemistry vol. 136 pp. 397-406 (Year: 1984).*

"ACTIVO-P11 Automated Peptide Synthesizer" downloaded from https://activotec.com/wp-content/uploads/2021/08/ACTIVO-P11-Brochure.pdf (Year: 2021).*

Knud J. Jensen et al. (eds.), Peptide Synthesis and Applications, Methods in Molecular Biology, vol. 1047, DOI 10.1007/978-1-62703-544-6_15, © Springer Science+Business Media New York, chapter 15 pp. 215-224 (Year: 2013).*

* cited by examiner

OLIGONUCLEOTIDE SYNTHESIZER

CROSS REFERENCE TO RELATED APPLICATIONS

This application claims the benefit of U.S. Provisional Patent Application No. 62/894,241, filed Aug. 30, 2019, incorporated herein by reference in its entirety.

FIELD

The disclosure relates to the field of devices and methods for chemical synthesis, analysis, and biological screening. In particular, the disclosure provides a new and improved apparatus for synthesizing oligonucleotides.

BACKGROUND

All existing solid-phase oligonucleotide synthesizers utilize high pressure pumps and a metal (usually stainless steel) closed column reactor. The closed column reactor is where the resin is filled and the reaction is performed. High pressure pumps are required to flow solvent and amidite solutions through the column reactor, as high back pressure can be generated. The method of mixing the solvents and amidite solution is by flowing through the column which contains the resin. The column is fixed in place, and the resin remains stationary within the column during this mixing process. The flow of the solvent and amidites only go in one direction.

Over the last 10 years, polystyrene or high load resin has gained popularity in utilization for solid-phase oligonucleotide synthesis. The existing synthesizers however have many challenges associated with utilizing polystyrene or high load resin, namely due to the amount of swelling and growth that occurs with these resins. Due to the swelling of the resin, significant back pressure can occur within the column as the resin begins to compress due to the flow of solvent. This back pressure can impede further flow and stop the synthesis. Due to the growth of the resin, the closed column reactors must calculate the amount of additional volume to account for resin growth, which is a manufacturing inefficiency.

SUMMARY

The disclosure provides a solid phase oligonucleotide synthesis reaction vessel. In one embodiment, the reaction vessel includes a housing defining a chamber containing a solid phase synthesis resin, the housing made of glass to allow for visualization of the reaction. In one embodiment, the vessel includes an operable inlet and outlet port for fluid (both gas and liquid) communication with said chamber. In one embodiment, the housing has the appropriate volume to contain both the solid phase synthesis resin, as well as additional volume for resin growth. In one embodiment, the reaction vessel includes filter plates to enable filtered fluid flow both in and out of the chamber from the exterior, as well as maintain the solid phase synthesis resin within the chamber during fluid transfer. In one embodiment, the reaction vessel includes a fixture that holds the filter plates in place, preventing dislodgement of the filter during fluid flow into the chamber. In one embodiment, the reaction vessel includes a housing that allows for the reaction vessel to be held by a clamp. In one embodiment, the inlet and outlet port for fluid communication is connected to different valve mechanisms and a control system which allows for gas and liquid communication. In one embodiment, the gas communication is connected to a pressure regulator and flow control, to allow for adjustable precision control of gas rate into the housing chamber to bubble the resin within the reaction vessel for mixing.

The disclosure also provides a solid phase oligonucleotide synthesizer mixer. In one embodiment, the synthesizer mixer includes comprising an invertible fixture which holds a reaction vessel described herein, whereas the invertible fixture is connected to a shaft that can axially rotate. In one embodiment, the shaft is connected to a pneumatic or electrical actuator, which powers the shaft to axially rotate. In one embodiment, the pneumatic or electrical actuator is connected to a control system, which can determine the rate of rotation.

The disclosure also provides a solid phase oligonucleotide synthesizer mixer. In one embodiment, the solid phase oligonucleotide synthesizer mixer includes comprising a housing defining a chamber containing a solid phase synthesis resin. In one embodiment, the housing is made of glass to allow for visualization of the reaction, and contains a multiple operable inlet and outlet port for fluid (both gas and liquid) communication with the chamber. In one embodiment, the housing has a port for a stir shaft to enter the chamber, and the port containing a seal around the stir shaft. In one embodiment, the stir shaft is connected to a motor which allows for axial rotation of the stir shaft, and the stir shaft within the reaction vessel chamber has agitator blades connected to the stir shaft to allow for mixing of the resin. In one embodiment, during mixing with said mixers, the operable inlet and outlet port for fluid communication are connected to a pump and in a loop, allowing fluid circulation. In one embodiment, the fluid path goes out of the outlet port and back into the inlet port. In one embodiment, during mixing with said mixers, the operable inlet and outlet port for fluid communication are connected to a pump and the inlet port is connected to a solvent reservoir to deliver solvent, and the outlet port is connected to a waste reservoir, and the pump is on allowing for fluid to flow from the solvent reservoir, through the reaction vessel, and to the waste reservoir.

The disclosure also provides a low cross link resin for a high swelling resin in ACN and toluene. In one embodiment, the low cross link resin has a higher substitution between 0.3 to 0.8 mmol/g. In one embodiment, the resin has a large pore size between 300 Å to 1000 Å to facilitate more space for oligo chain growing on resin. In one embodiment, the cross link resin is in the 1% to 3% level. In one embodiment, the resin can shrink in MeOH to ease the final cleavage.

BRIEF DESCRIPTION OF THE DRAWINGS

The foregoing summary, as well as the following detailed description, will be better understood when read in conjunction with the appended drawings.

DETAILED DESCRIPTION

Figure 1:
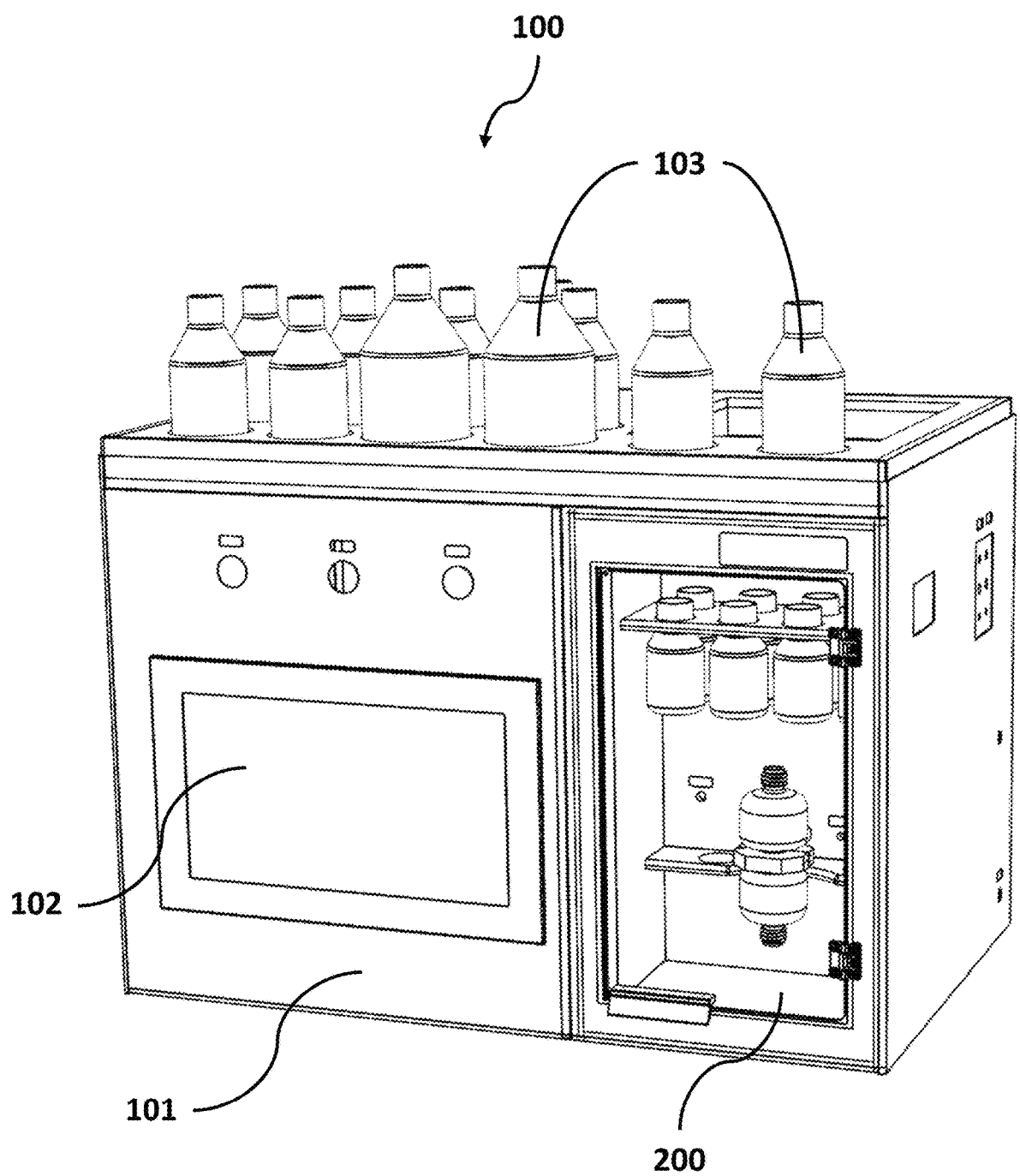
FIG. 1 is a perspective front view of an oligonucleotide synthesizer.

The disclosure provides an oligonucleotide synthesizer for solid-phase synthesis that consists of an open space glass reactor, a novel mixing methods to prevent resin compression and provide high performance mixing, and a low cross link resin. The key novel aspect of this oligonucleotide synthesizer as compared to current oligonucleotide synthesizers, is that current systems all maintain the resin in a stationary state with a fixed column, and the mixing is performed by flowing the solvent past the stationary resin. The disclosed oligonucleotide synthesizer agitates the resin and solvent to perform the mixing, with various methods of agitating the resin and solvent, including, without limitation, inversion, overhead stirring, bubbling, etc.

Reference will now be made in detail to the preferred embodiments of the disclosure, examples of which are illustrated in the accompanying drawings. While the disclosure will be described in conjunction with the preferred embodiments, it will be understood that they are not intended to limit the disclosure to those embodiments. On the contrary, the disclosure is intended to cover alternatives, modifications and equivalents, which may be included within the spirit and scope of the disclosure as defined by the appended claims.

As used herein, the terms "nucleic acid" or "oligonucleotide," and other grammatical equivalents herein, referred to at least two nucleotides covalently linked together. A nucleic acid of the present disclosure will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114: 1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. In addition nucleic acids include, "locked nucleic acids" such as those described in Koshkin et al., J. Am. chem. Soc. 120: 13252-3 (1998). All of these references are hereby expressly incorporated by reference.

Oligonucleotides, and nucleic acids in general, can be synthesized using a variety of possible synthetic reactions. In some embodiments, phosphoramidite chemistry is used, with enzymatic techniques and techniques based on photodeprotection useful as well. In addition, any number of nucleic acid analogs and labeled nucleic acids can be made and used. See for example Oligonucleotides and Analogs: A Practical Approach, Ed. F. Eckstein, IRL Press, 1991, hereby incorporated by reference in its entirety. One should appreciate however that the present disclosure is similarly applicable to other chemical protocols having similar functional steps. For example, components of the present disclosure can be applied to appropriate liquid-phase, combinatorial chemistry synthesis protocols, to other solid- or liquid-phase chemical protocols, or to any combination thereof.

As used herein, the term "protein" includes proteins, polypeptides, and peptides. The protein may be made up of naturally occurring amino acids and peptide bonds, or synthetic peptidomimetic structures. The side chains may be in either the (R) or the (S) configuration. In a preferred embodiment, the amino acids are in the (S) or L-configuration. If non-naturally occurring side chains are used, non-amino acid substituents may be used, for example to prevent or retarded in vivo degradations. Proteins can be synthesized using the methods and apparatus of the present disclosure using standard techniques.

The disclosure provides an oligonucleotide synthesizer including a reaction vessel assembly including a reaction vessel, wherein the reaction vessel holds an oligonucleotide solid phase synthesis resin and a liquid phase. In some embodiments, the oligonucleotide solid phase synthesis resin includes a plurality of discrete resin pieces. In some embodiments, the plurality of discrete resin pieces includes a plurality of resin beads. In some embodiments, the reaction vessel assembly further includes a reaction vessel bracket. In some embodiments, the reaction vessel bracket is a hinged bracket or a tension bracket. In some embodiments, the reaction vessel assembly further includes a rotation actuator. In some embodiments, the reaction vessel assembly further includes a rotation shaft. In some embodiments, the reaction vessel assembly further includes an overhead stirring assembly. In some embodiments, the reaction vessel includes one or more chambers. In some embodiments, the v/v ratio between the plurality of discrete resin pieces and the liquid phase allows for mechanical stirring of the plurality of discrete resin pieces.

The disclosure also provides a solid phase oligonucleotide synthesis reaction vessel including a housing defining a chamber containing a solid phase synthesis resin, and an operable inlet port and an outlet port for fluid communication with said chamber. In some embodiments, the fluid is gas, liquid, or both. In some embodiments, the housing is made of glass to allow for visualization of the reaction. In some embodiments, the housing has a volume allowing for the solid phase synthesis resin and for additional volume for resin growth. In some embodiments, the solid phase oligonucleotide synthesis reaction vessel further includes one or more filter plates. In some embodiments, the filter plates enable filtered fluid flow both in and out of the chamber from the exterior. In some embodiments, the filter plates maintain the solid phase synthesis resin within the chamber during fluid transfer. In some embodiments, the solid phase oligonucleotide synthesis reaction vessel further includes one or more fixtures for holding the filter plates in place and preventing dislodgement of the filter plates during fluid flow into the chamber. In some embodiments, the disclosure provides an oligonucleotide synthesizer including a solid phase oligonucleotide synthesis reaction vessel described herein. In some embodiments, the oligonucleotide synthesizer further includes a housing and a clamp holding the reaction vessel. In some embodiments, the inlet and outlet ports for fluid communication are connected to different valve mechanisms and a control system which allows for gas and liquid communication. In some embodiments, the gas communication is connected to a pressure regulator and flow control, to allow for adjustable precision control of gas rate into the housing chamber to bubble the resin within the reaction vessel for mixing.

The disclosure also provides a solid phase oligonucleotide synthesizer mixer including an invertible fixture which holds the reaction vessel, whereas the invertible fixture is connected to a shaft that can axially rotate. In some embodiments, the shaft is connected to a pneumatic or electrical actuator, which powers the shaft to axially rotate. In some embodiments, the pneumatic or electrical actuator is connected to a control system, which can determine the rate of rotation.

The disclosure also provides a solid phase oligonucleotide synthesizer mixer including a housing defining a chamber containing a solid phase synthesis resin, whereas said housing is made of glass to allow for visualization of the reaction, and contains an multiple operable inlet and outlet port for fluid (both gas and liquid) communication with said chamber. In some embodiments, the housing has a port for a stir shaft to enter the chamber, and said port contains a seal around the stir shaft. In some embodiments, the stir shaft is connected to a motor which allows for axial rotation of the stir shaft, and the stir shaft within the reaction vessel chamber has one or more agitator blades connected to the stir shaft to allow for mixing of the resin. In some embodiments, during mixing with said mixers, the operable inlet and outlet port for fluid communication are connected to a pump and in a loop, allowing fluid circulate whereas the fluid path goes out of the outlet port and back into the inlet port. In some embodiments, during mixing with said mixers, the operable inlet and outlet port for fluid communication are connected to a pump and the inlet port is connected to a solvent reservoir to deliver solvent, and the outlet port is connected to a waste reservoir, and the pump is on allowing for fluid to flow from the solvent reservoir, through the reaction vessel, and to the waste reservoir.

The disclosure also provides a low cross link resin for a high swelling resin in acetonitrile (ACN) and toluene, wherein the low cross link resin had a higher substitution between 0.3 to 0.8 mmol/g. In some embodiments, the resin has a pore size between about 300 Å to 1000 Å to facilitate more space for oligo chain growing on resin. In some embodiments, the cross link resin is in the 1% to 3% level. In some embodiments, the resin can shrink in MeOH to ease the final cleavage.

Figure 2:
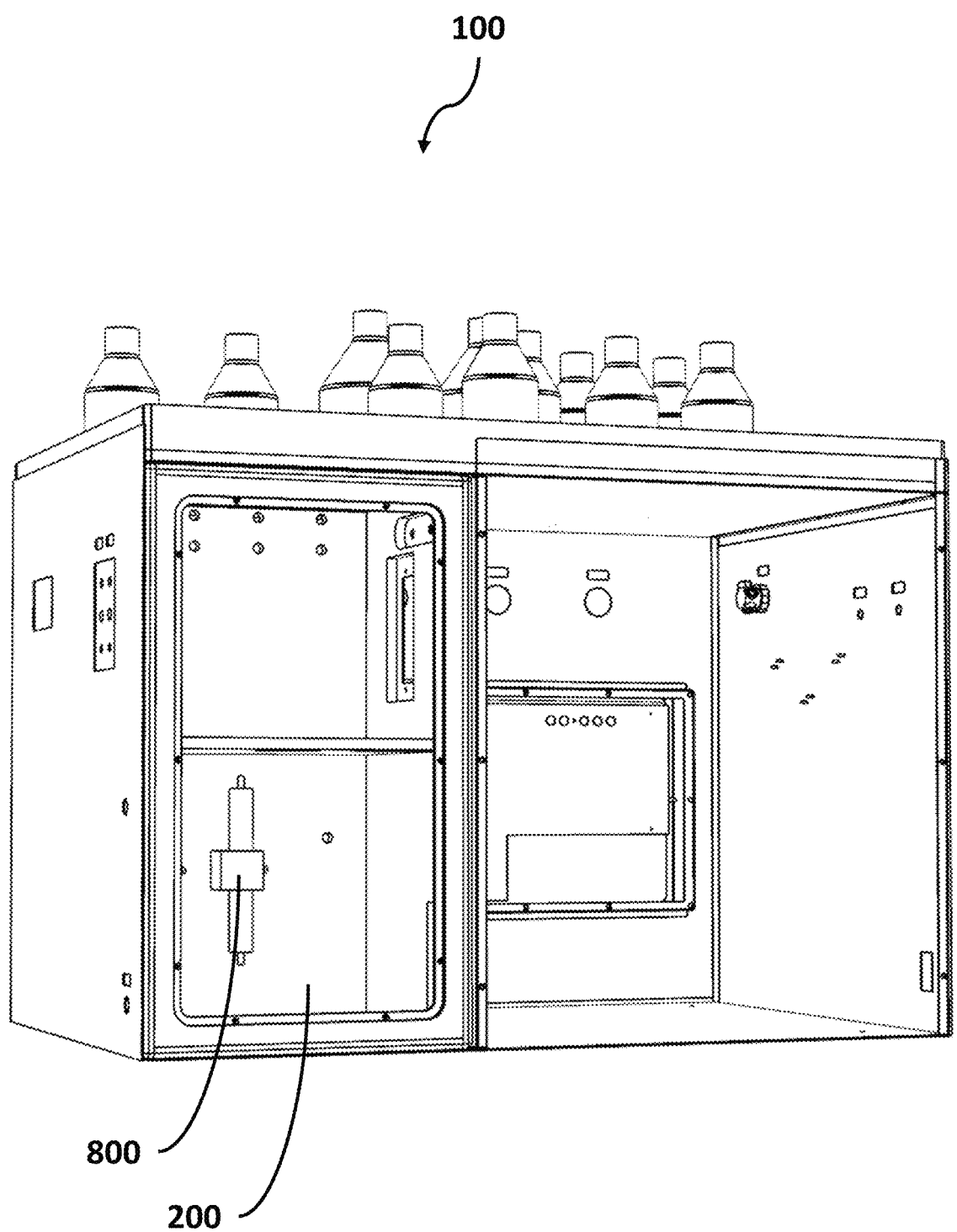
FIG. 2 is a perspective back view of an oligonucleotide synthesizer.

Referring to the figures, FIG. 1 is a perspective front view of an oligonucleotide synthesizer 100. The synthesizer includes a body 101, which may include an chassis, a frame, or any other similar structural elements. The synthesizer provides for holding areas for solvent and/or reagent bottles and containers 103. In some embodiments, such bottles or containers may be placed at the top of the synthesizer for ease of access. The synthesizer includes a screen 102, which can be without limitation any type of screen for providing an user interface, for example a touch screen. Any other user interface devices may be included, for example a mouse, a keyboard, or the like, whether hard wired or wirelessly connected. The synthesizer also includes a reaction vessel enclosure 200. Turning to FIG. 2, in a back perspective view of the synthesizer 100, the back of the reaction vessel enclosure 200 can also be seen, including a pneumatic or electrical actuator that can move the reaction vessel as described herein.

The synthesizer includes a computer with a system software for controlling all systems and parts of the synthesizer such as valves, pumps, pressure sensors, detectors, etc. Such computer may include one or more processing units (CPU's), a network or other communications interface, a memory (e.g., random access memory), one or more magnetic disk storage and/or persistent devices optionally accessed by one or more controllers, one or more communication busses for interconnecting the aforementioned components, a user interface, the user interface including a display and input (e.g., keyboard, keypad, touch screen), and a power supply for powering the aforementioned components. In some embodiments, data in memory is seamlessly shared with non-volatile memory using known computing techniques such as caching. In some embodiments, memory includes mass storage that is remotely located with respect to the central processing unit(s). In other words, some data stored in the memory may in fact be hosted on computers that are external to the synthesizer computer, but that can be electronically accessed over an Internet, intranet, or other form of network or electronic cable using a network interface.

Figure 3:
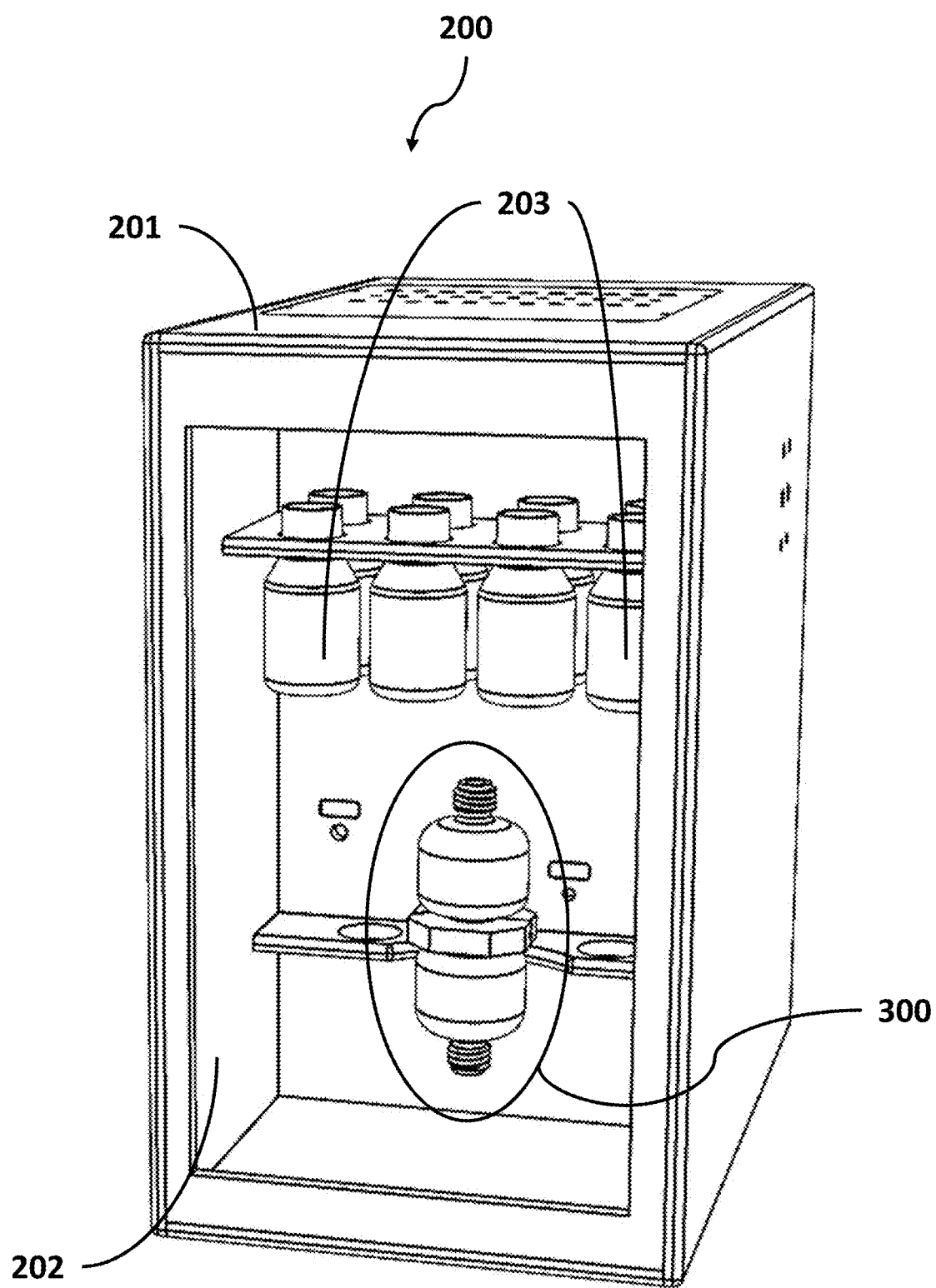
FIG. 3 is a perspective front view of a reaction vessel enclosure of an oligonucleotide synthesizer.
Figure 16:
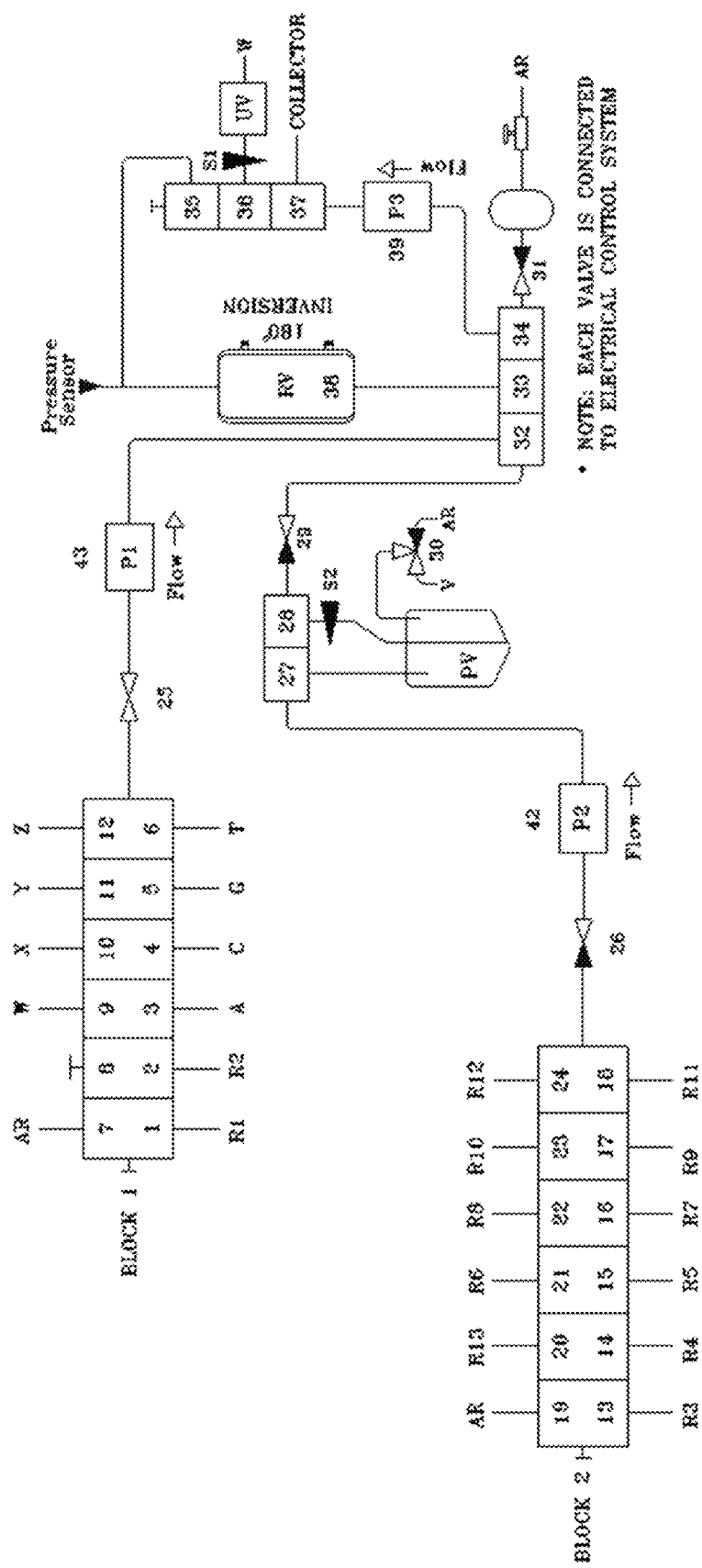
FIG. 16 is a flowchart of an oligonucleotide synthesizer.

FIG. 3 illustrates a perspective front view of the reaction vessel enclosure 200 of an oligonucleotide synthesizer described herein. The enclosure includes a case 201 and a front door 202, which preferably is made of a transparent material such as glass or a thermoplastic material. One or more solvent or reagent bottles 203 are included in the enclosure and can be connected with other components of the synthesizer according to the flowchart in FIG. 16. The reaction vessel assembly enclosure includes reaction vessel assembly 300.

Figure 4:
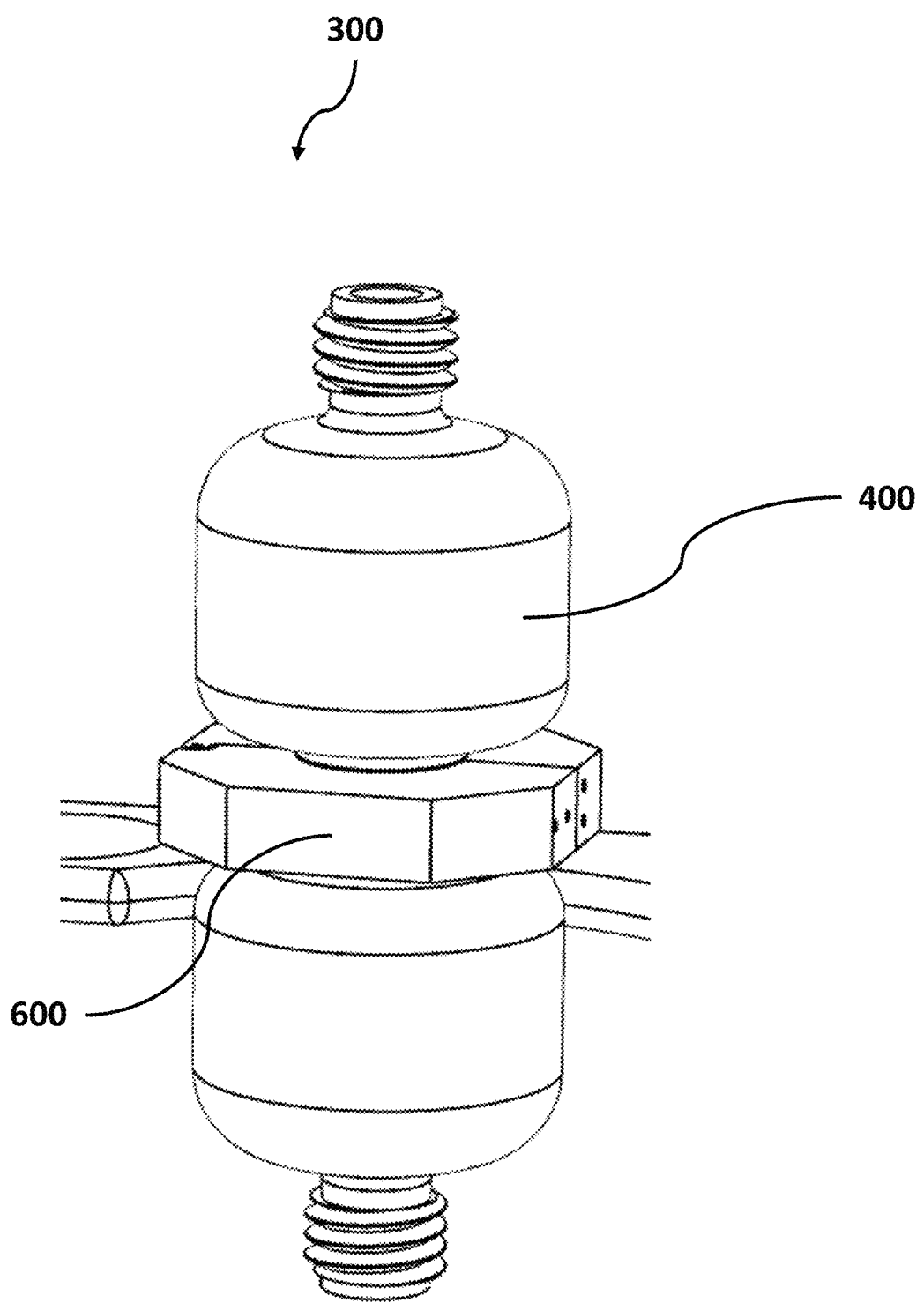
FIG. 4 is a perspective view of a reaction vessel assembly.
Figure 5:
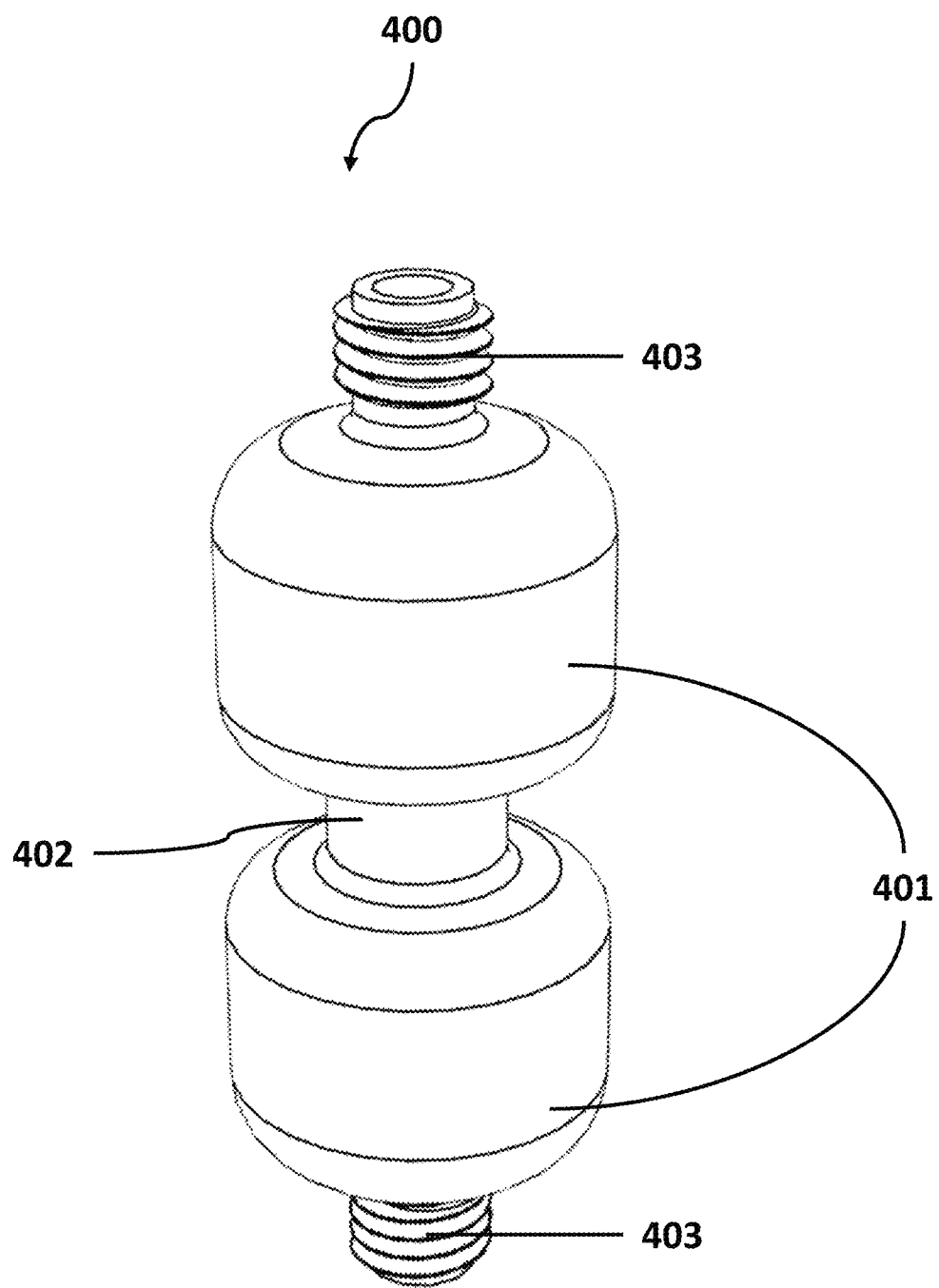
FIG. 5 is a perspective view of a multi chamber reaction vessel.
Figure 6:
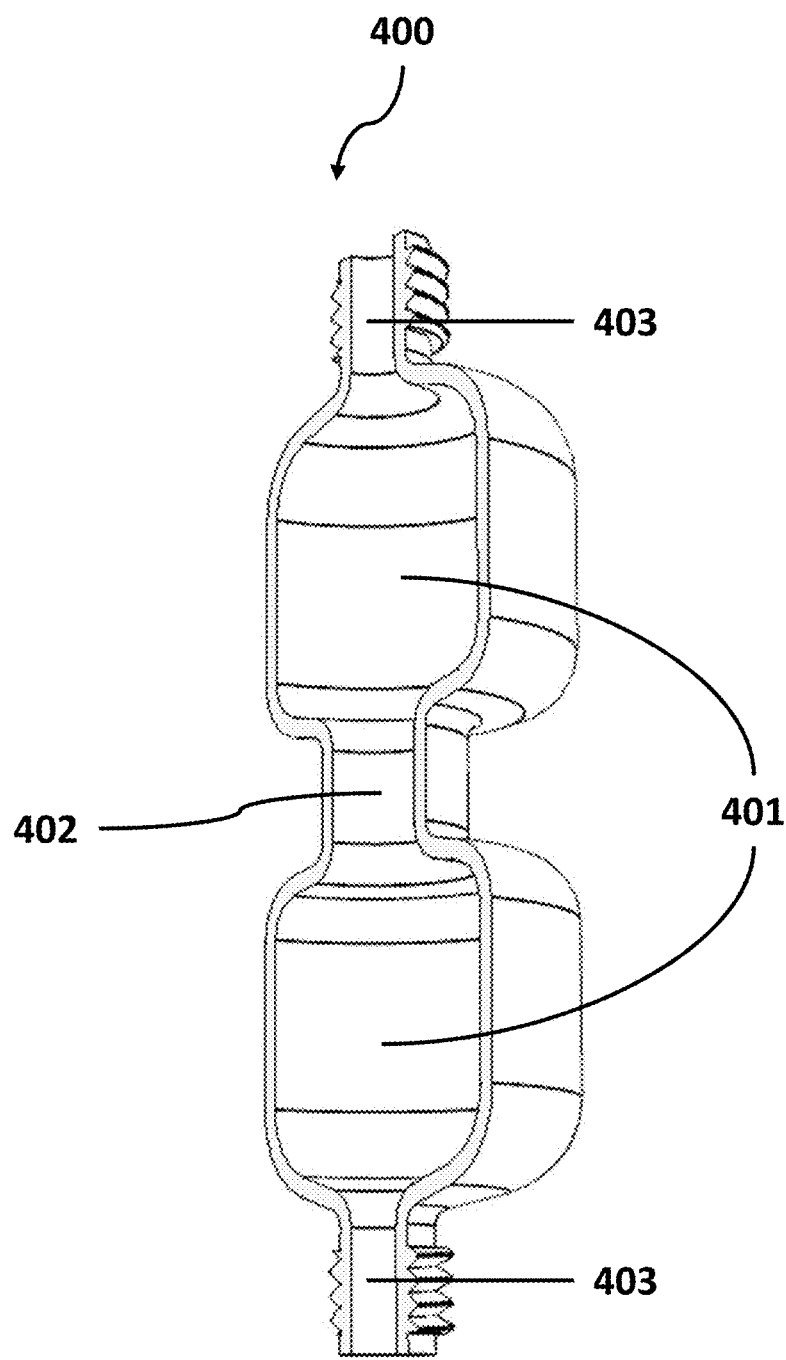
FIG. 6 is a sectional view of a multi chamber reaction vessel.

FIG. 4 illustrates a perspective view of reaction vessel assembly 300, including reaction vessel 400 and reaction vessel holder 600. Turning to FIGS. 5 and 6, reaction vessel 400 has two distinct chambers 401. More than two chambers are possible. A reaction vessel chamber 401 is connected with another reaction vessel chamber through a narrower connecting passage 402. Generally, the reaction passage 402 is designed to allow passage of solvent, and/or solid phase synthesis support material, for example solid phase synthesis beads, from one chamber to another upon movement of the reaction vessel. For example, if reaction vessel 400 is tipped at a certain angle from a resting position, then material including solid phase synthesis support material will pass from one chamber to another. The reaction vessel 400 includes connecting features for inserting the reaction vessel into a flow path such as the flow path described in FIG. 16. In some embodiments, the connecting features include threaded tubular ends 403, each able to function as an inlet or outlet connection to a flow path.

Figure 7:
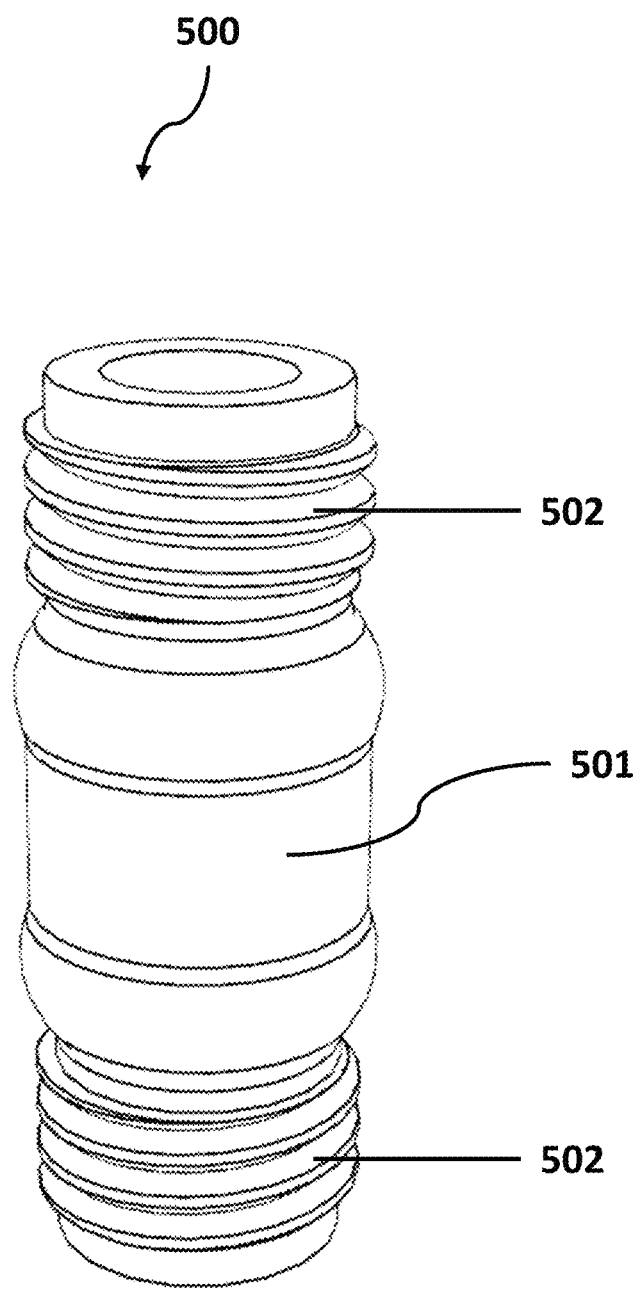
FIG. 7 is a perspective view of a single chamber reaction vessel.
Figure 8:
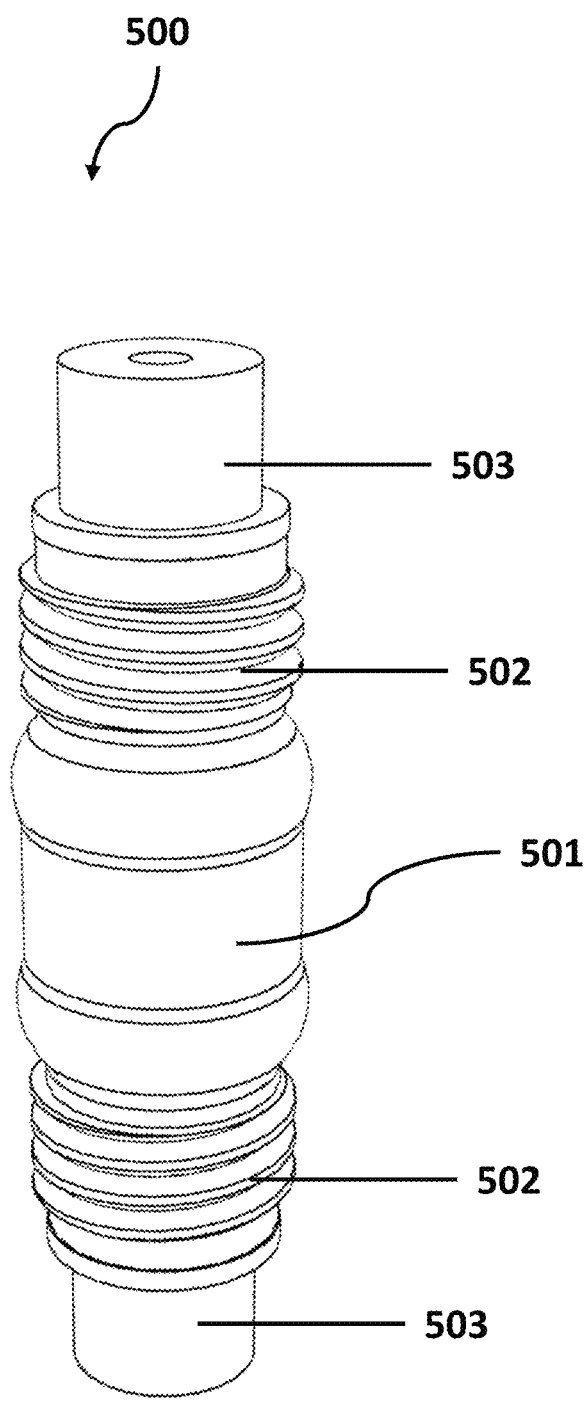
FIG. 8 is a perspective view of a single chamber reaction vessel fitted with end fixtures.
Figure 9:
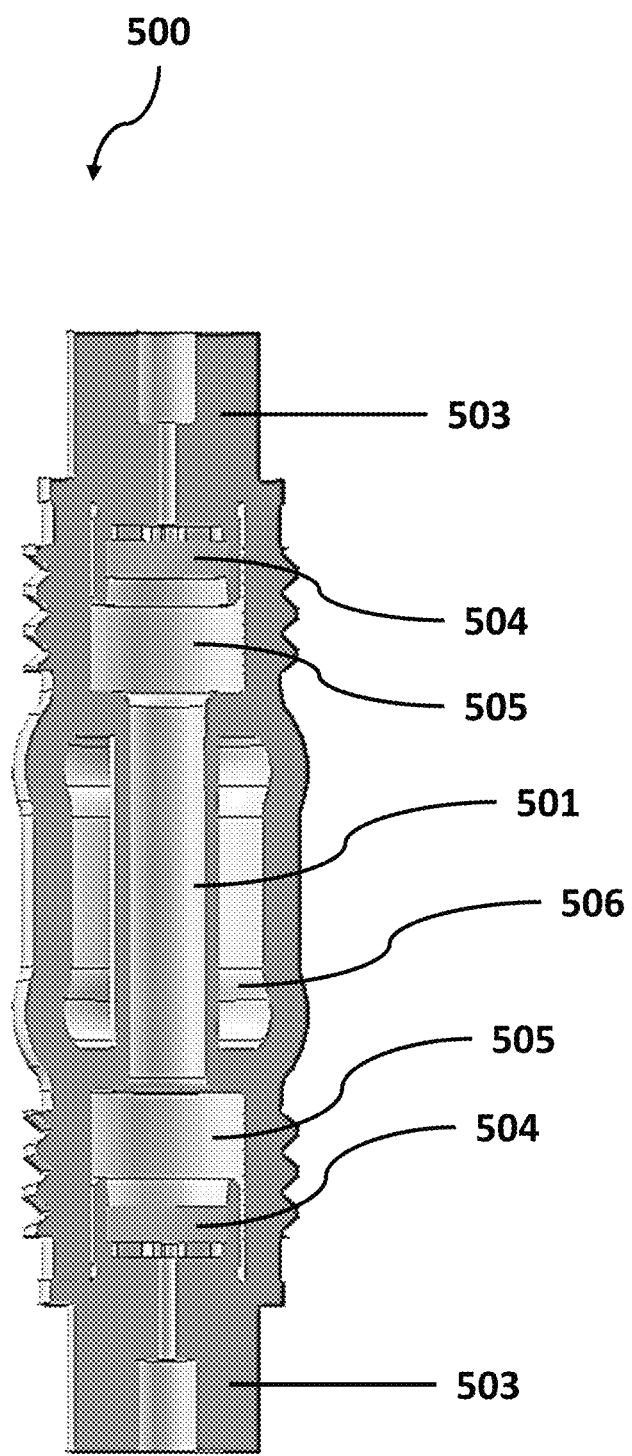
FIG. 9 is a sectional view of a single chamber reaction vessel fitted with end fixtures and filter plates.

Turning to FIGS. 7-9, single chamber reaction vessel 500 is also disclosed herein. Similar to a multi chamber reaction vessel 400, a single chamber reaction vessel can be moved, for example tipped at an angle from a resting position, to allow moving of material included therein, for example a solid phase synthesis material, within the reaction vessel. A single chamber reaction vessel 500 includes a reaction chamber 501 and tubular threaded ends 502 allowing for connecting the reaction vessel into a flow path such as the flow path described in FIG. 16. The volume of the reaction chamber 501 is sufficient to contain a solid phase synthesis support resin, including a volume allowance for resin swell with solvent. As shown in FIG. 9, the reaction vessel may have a reinforcing space and additional enclosure 506 for mechanical support when the reaction vessel is placed in a reaction vessel holding bracket. All reaction vessels described herein can be made of any material, including a transparent material allowing for visualization of the material in the reaction vessel.

As shown in FIGS. 8 and 9, a reaction vessel can be fitted with end fixtures 503 that can be inserted over an inlet/outlet ports 505. The fixtures 503 can hold in place inlet/outlet filters 504.

Figure 10:
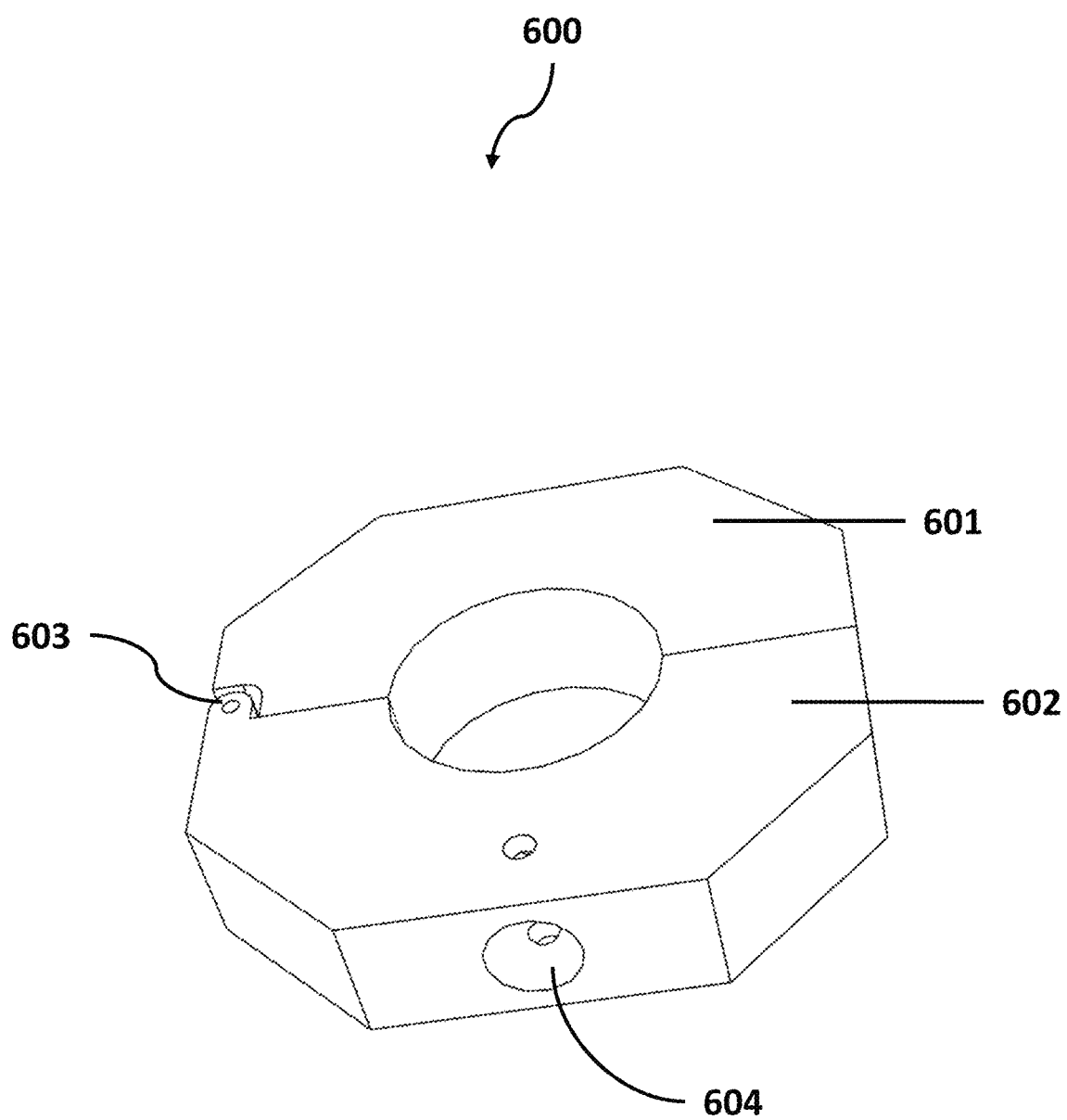
FIG. 10 is a perspective view of a hinged bracket for holding a reaction vessel in a reaction vessel assembly.
Figure 11:
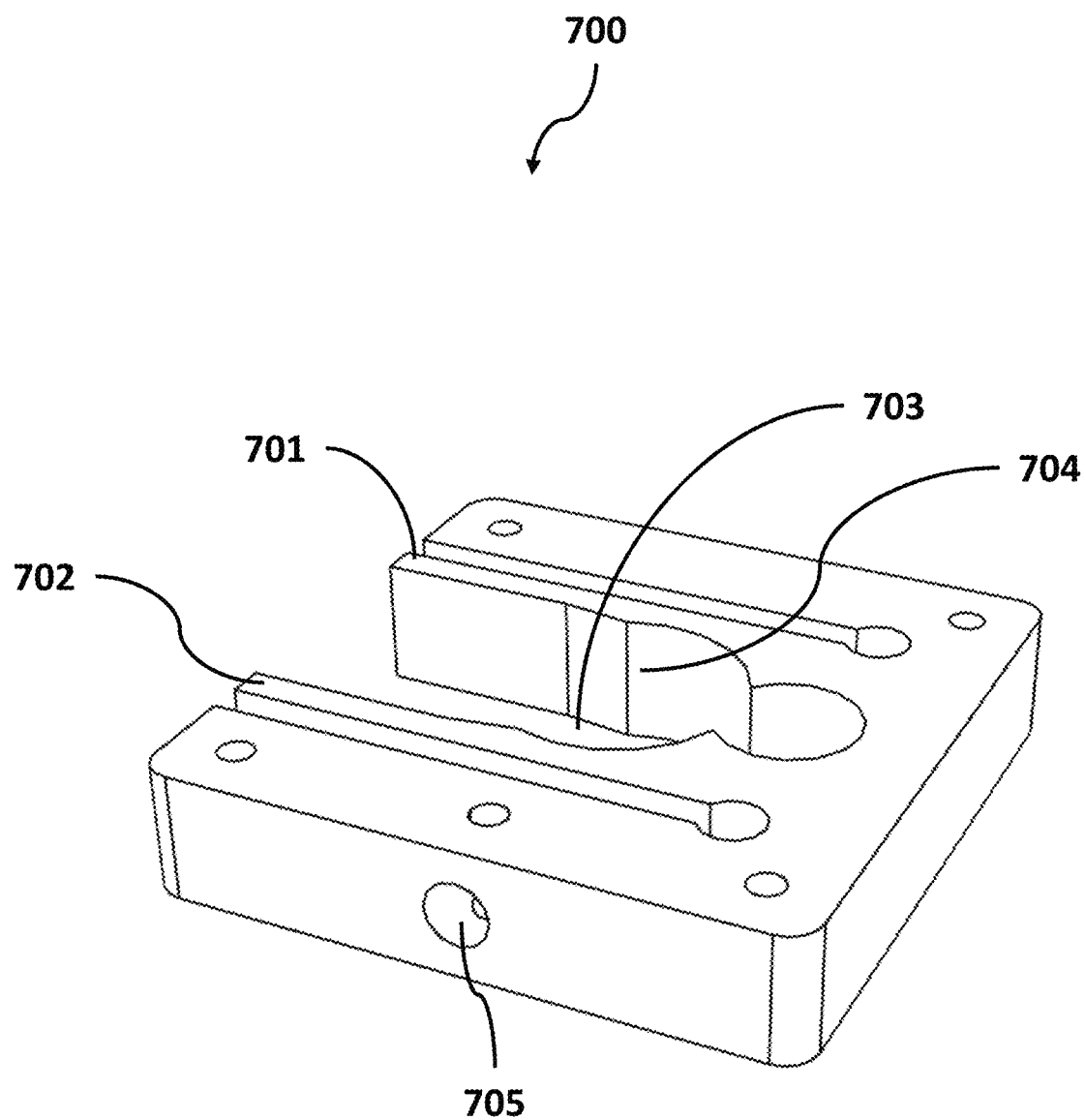
FIG. 11 is a perspective view of a tension bracket for holding a reaction vessel in a reaction vessel assembly.

Shown in FIGS. 10 and 11 are perspective views of reaction vessel holding brackets. Holding bracket 600 (FIG. 10) includes two semi-brackets 601 and 602 connected through a hinge 603. The bracket includes a connecting feature which can connect the bracket to an axle or a shaft that can move the bracket around an axis. For bracket 600 this connecting feature is an opening 604 where an axle or shaft can be inserted.

Turning to FIG. 11, a reaction vessel tension holding bracket 700 includes two retaining features 701 and 702 that can move into adjacent relief features upon inserting a reaction vessel between the two features, wherein a dimension of the reaction vessel (e.g., a diameter) is slightly larger than the distance between features 701 and 702. The reaction vessel can be pushed between the two features toward holding opening 703. Once the reaction vessel is pushed past the one or more notches 704, the reaction vessel will be temporarily or permanently retained in the holding opening 703 of a hinged bracket for holding a reaction vessel in a reaction vessel assembly. The tension bracket 700 includes a connecting feature which can connect the bracket to an axle or a shaft that can move the bracket around an axis. For bracket 700 this connecting feature is an opening 705 where an axle or shaft can be inserted.

Figure 12:
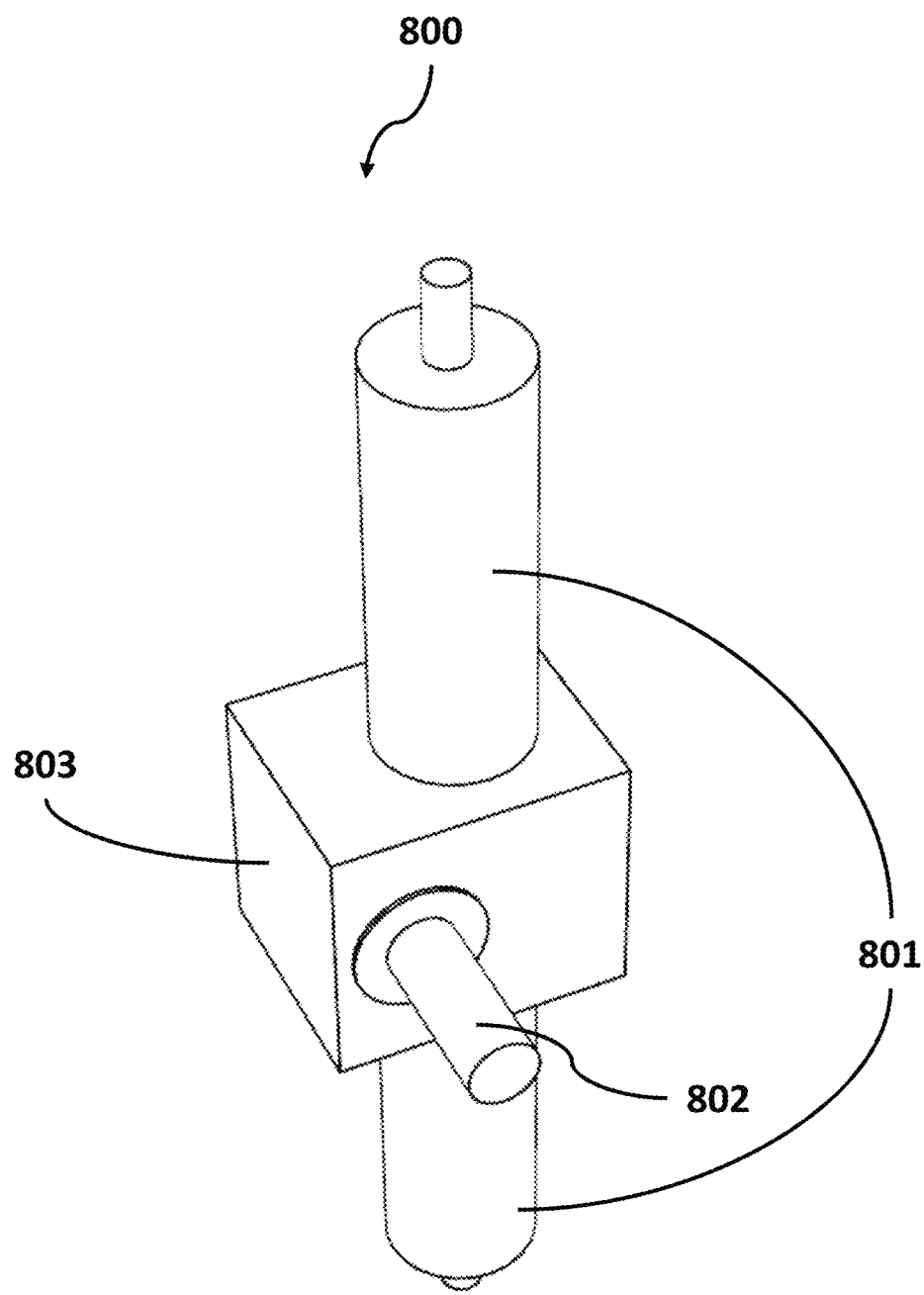
FIG. 12 is a perspective view of a rotation actuator.

Turning to FIG. 12, a perspective view of a rotation actuator is shown. The actuator includes one or more axles 801 and 802. In some embodiments, the actuator may convert one rotational motion into another rotational motion through a gear box 803, which can include any type of gear (e.g., a worm gear).

Figure 13:
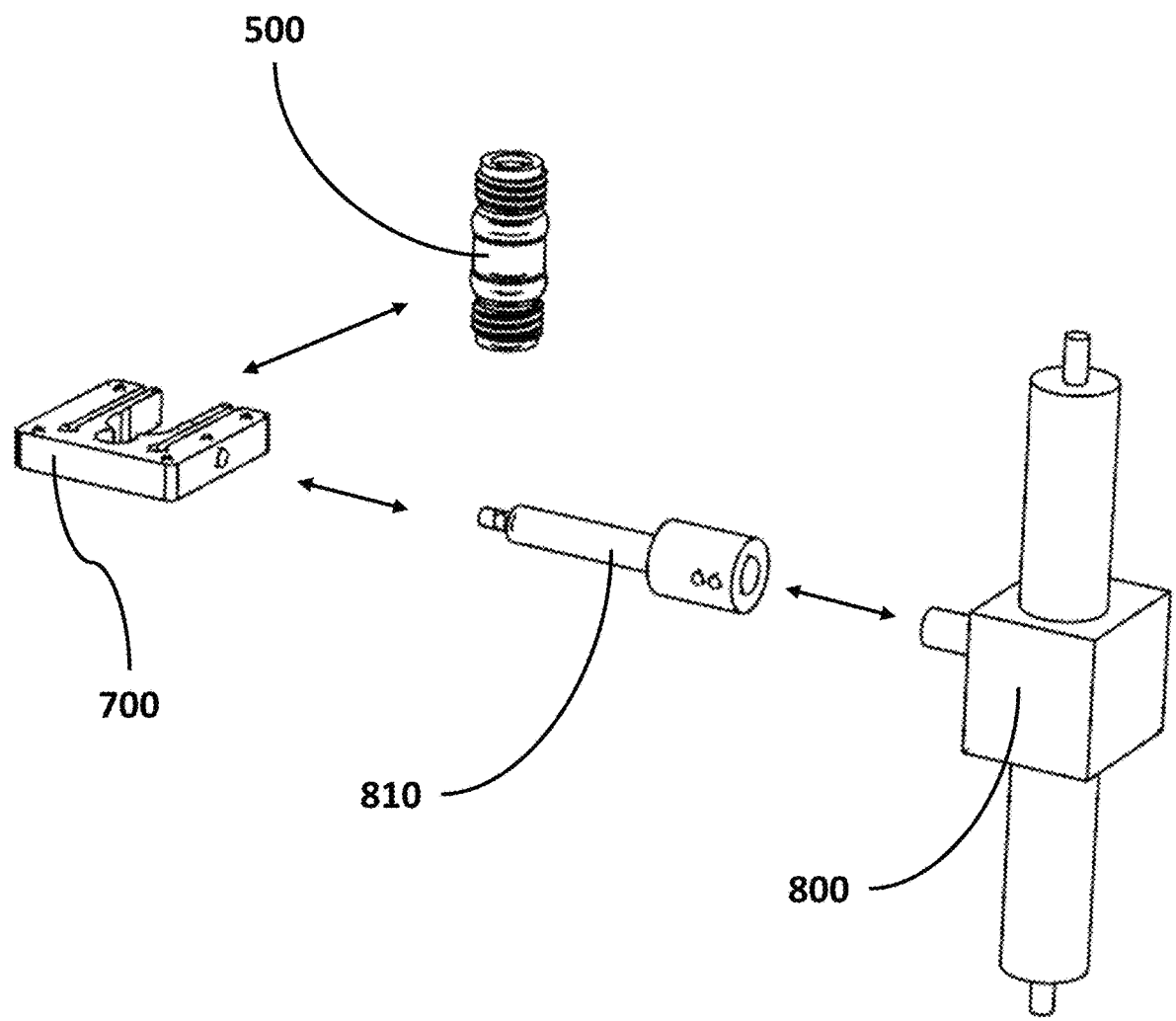
FIG. 13 is an exploded view of a reaction vessel assembly including a reaction vessel, a holding bracket, a rotation actuator, and a rotation shaft.

Turning to FIG. 13, an exploded view of a reaction vessel assembly including a reaction vessel, a holding bracket, a rotation actuator, and a rotation shaft is shown. Reaction vessel 500 is placed in reaction vessel holding bracket 700 (a tension bracket is shown here, but any other bracket can be used). In turn, reaction vessel holding bracket 700 is connected to a axial rotation shaft 810, which in turn is connected to actuator 800.

Figure 14:
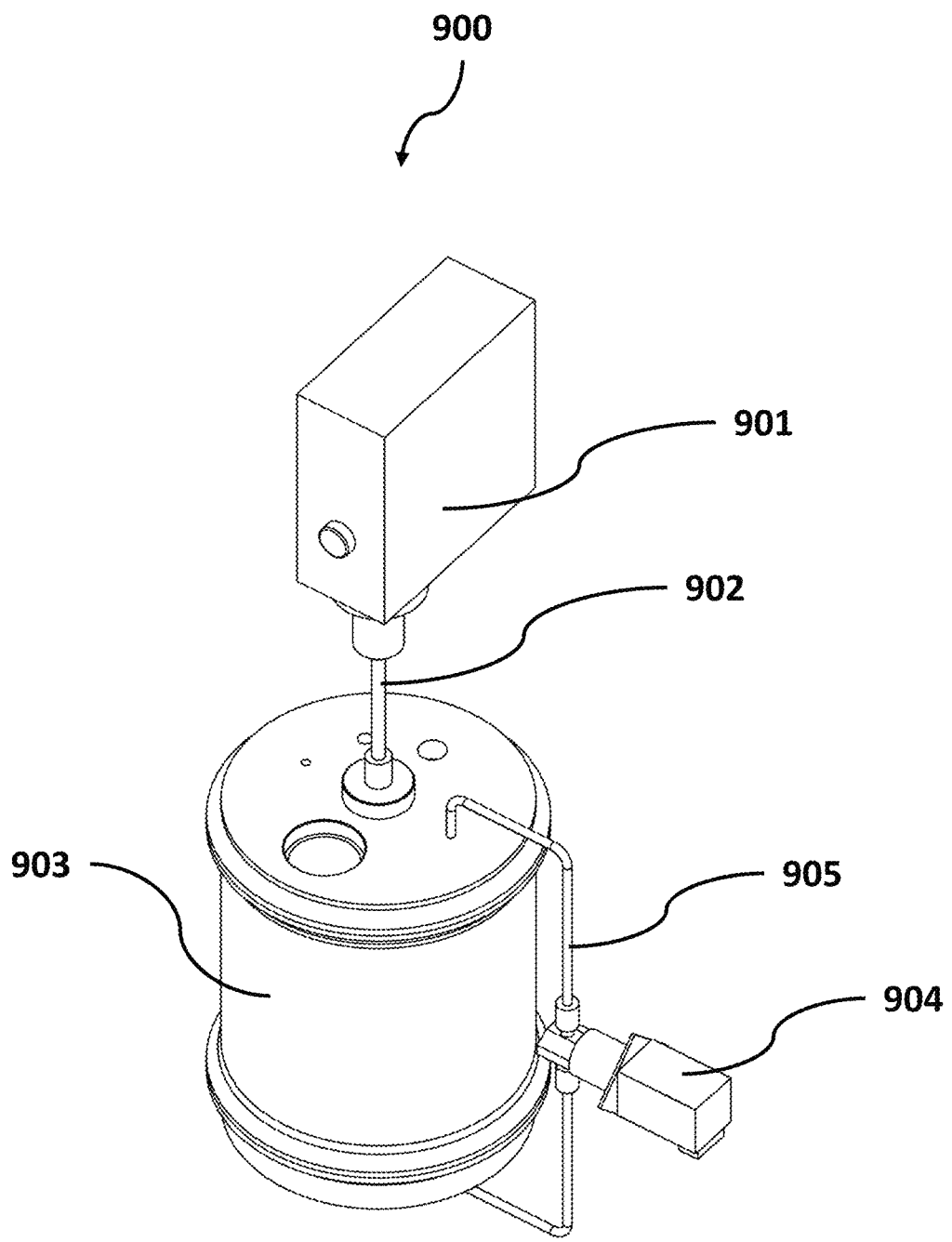
FIG. 14 is a perspective view of a reaction vessel assembly including an overhead stirring assembly.
Figure 15:
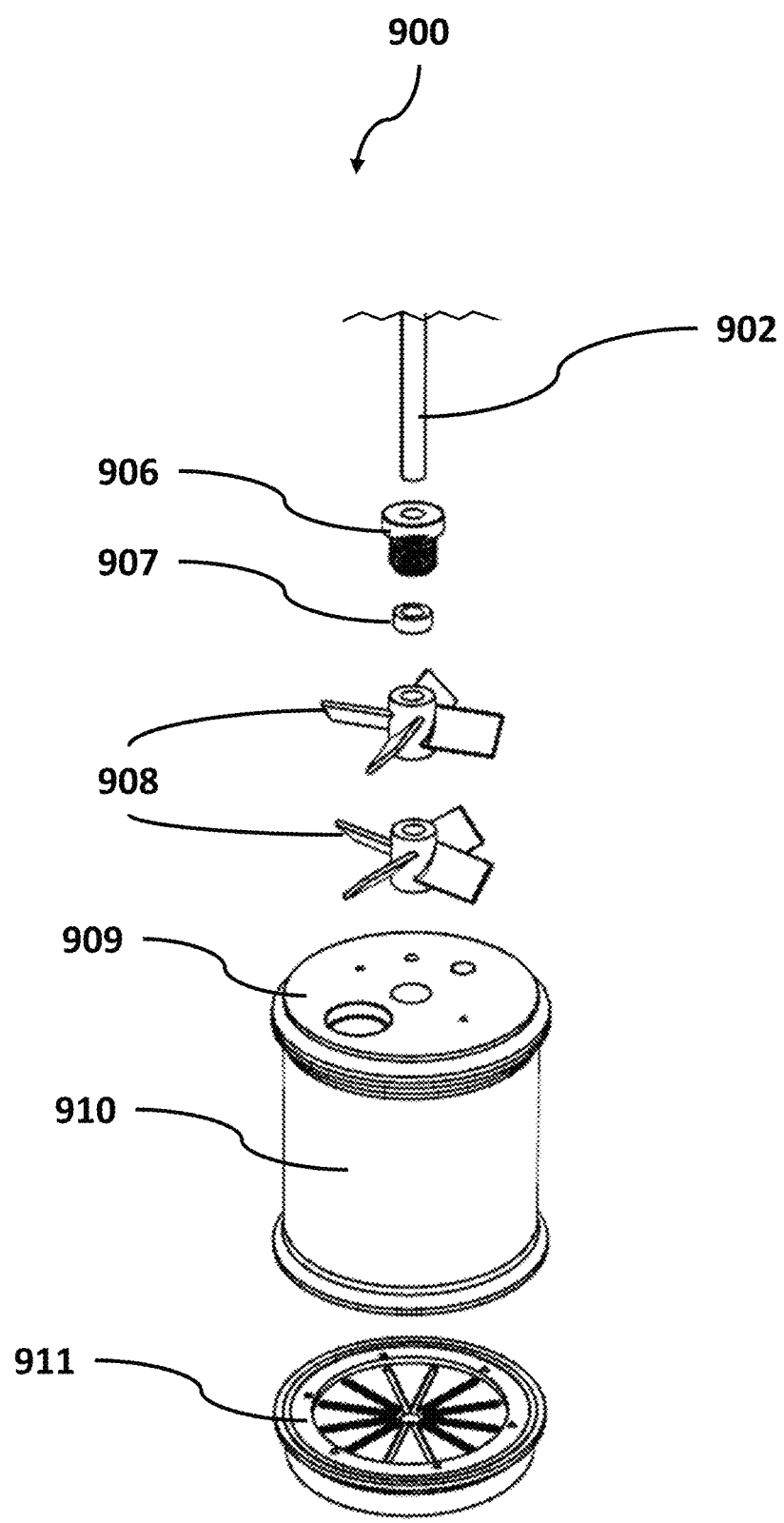
FIG. 15 is an exploded view of a reaction vessel assembly including an overhead stirring assembly.

In some embodiments, the synthesizer can include a reaction vessel assembly where the mechanical stirring of the solid synthesis support is achieved through traditional overhead stirring rather than moving the reaction vessel. Turning to FIG. 14, a perspective view of a reaction vessel assembly 900 including an overhead stirring assembly is shown. The assembly includes a reaction vessel 903. The assembly also includes stirring motor 901, a stir shaft 902, a pump 904, and one or more fluid circulation features such as tubing, connecting the pump to the reaction vessel. As shown in FIG. 15 in an exploded view of a reaction vessel assembly 900 including an overhead stirring assembly, the stir shaft 902 is inserted into the reaction vessel through one or more holders and seals 906 and 907, and has attached at the end inside the reaction vessel one or more agitator blades 908. The reaction vessel 903 includes a side wall 910, a top end 909 having one or more openings for inserting the stir shaft or attaching various tubing elements, and a bottom end 911 likewise having one or more openings for attaching various tubing elements. All elements of reaction vessel 903, including side wall 910, top end 909, and bottom end 911, can be made of any material, including a transparent material such as glass to allow for reaction visualization.

As described herein, the synthesizer utilizes solid phase synthesis chemistry to manufacture oligonucleotides. The instrument has multiple features to accomplish this that includes, without limitation, one or more of: delivery of multiple reagents in liquid form from reagent reservoirs to the reaction vessel; delivery of multiple reagents into a vessel which can be used to mix the reagents prior to delivery to the reaction vessel; purging of argon at a steady state flowrate with a needle valve to maintain an inert atmosphere for all reservoirs and reaction vessel; allowing for delivery of reagents with metering controlled to ensure specified volume of delivery; a mechanism which inverts the reaction vessel to allow for the resin and solvent inside to agitate and mix; a UV detector that is connected to the waste stream to detect the UV absorbance of the fluid exiting the synthesizer; a pressure sensor to detect the pressure in which the reaction vessel is under throughout the synthesis; a pump connecting the solvent reservoirs to the reaction vessel and subsequently to the waste line, to allow for solvents to deliver to the reaction vessel and flow through the reaction vessel and go directly to waste; a pump that allows for flow from the outlet of the reaction vessel back to the inlet of the reaction vessel, allowing for circulation of the solvent within the reaction vessel; a specific configuration of the pumps and valves, where delivery of the amidites to the reaction vessel is through one valve block and pump, and the reagents are delivered through a separate valve block and pump to the reaction vessel, as to prevent cross contamination and ability for cleaning of the valves and line prior to subsequent reagent and amidite delivery.

The disclosure also provides a process for making an oligonucleotide, including reacting a oligonucleotide precursor with a solid phase support, and mechanically stirring the solid phase support. In some embodiments, the process further includes one or more activation steps. In some embodiments, the process further includes one or more coupling steps. In some embodiments, the process further includes one or more capping steps. In some embodiments, the process further includes one or more oxidation steps. In some embodiments, the process further includes one or more detritylation steps. In some embodiments, the process further includes one or more cleavage steps. In some embodiments, the process further includes one or more deprotection steps. In some embodiments, the solid phase support includes a plurality of discrete resin pieces. In some embodiments, the plurality of discrete resin pieces includes a plurality of resin beads. In some embodiments, the mechanical stirring of the solid phase support includes the motion of a reaction vessel including the solid support relative to a chassis, frame, or support. In some embodiments, the motion includes one or more of tipping, rocking, shaking, and inverting the reaction vessel relative to the chassis, frame, or support. In some embodiments, the mechanical stirring of the solid phase support includes stirring via a stir blade, a stir bar, or both. In some embodiments, the mechanical stirring of the solid phase support includes stirring via a plurality of bubbles moving relative to the solid phase support.

A synthesis protocol consists of a multitude of steps, including, without limitation, one or more steps selected from: delivery of reagents from "Block 2" (as labeled in the flowchart in FIG. 16) into the reaction vessel directly or first delivered into the pre-mix vessel for mixing prior to transfer to the reaction vessel; after multiple delivery of reagents that would allow for deprotection, capping, and washing steps in the synthesis, the coupling would be performed by delivery of amidite from "Block 1" to the reaction vessel; during the coupling step, the reaction vessel would invert multiple times over the coupling duration to allow the amidite solution and resin to agitate; upon completion of each of the steps where reagents or amidite solution is delivered to the reaction vessel, the reaction vessel would allow draining to the waste where the UV detector monitors the waste stream; drain to a collector is possible to allow for collection of the solution from the reaction vessel if a sample is desired.

In some embodiments, oligonucleotide solid phase synthesis includes the sequential addition of building blocks to intermediate, partially synthesized, compounds in order to synthesize a final compound. In solid-phase synthesis, final compounds are synthesized attached to solid-phase supports that permit the use of simple mechanical means to separate partially-synthesized intermediate compounds between synthetic steps. Typical solid-phase supports include microbeads having diameters from approximately 30 microns to 300 microns to which intermediate compounds covalently attach. Solid-phase synthesis typically proceeds according to one or more of the following steps. In a first step, reaction vessels are charged with a solid-phase support, typically a slurry of microbeads suspended in a solvent. In some embodiments, these microbeads are then preconditioned by incubating them in an appropriate solvent, and the first of the plurality of building blocks or a linker moiety is covalently linked to the microbeads. Subsequently, a plurality of building block addition steps are performed, all of which involve repetitive execution of the following or similar sub-steps, and in a sequence chosen to synthesize a desired compound. First, a sufficient quantity of a solution, which contains the building block moiety selected for addition, is dispensed into the reaction vessels so that the building block moiety is present in a molar excess to the intermediate compound present in the reaction vessel. A sub-step reaction is triggered and promoted by activating reagents and other reagents and solvents, which are also added to the reaction vessel. The reaction vessel is then incubated at a controlled temperature for a time, typically between 5 minutes and 24 hours, sufficient for the building block addition reaction to go to substantial completion. Optionally, during this incubation, the reaction vessels can be intermittently agitated, stirred, tipped, inverted, or a stream of gads bubbles could be introduced in the vessel in order to achieve mechanical stirring of the vessel's contents, including the solid phase support. Finally, in a last sub-step of building block addition, the reaction vessel containing the solid-phase support with attached intermediate compound is prepared for addition of the next building block by removing the spent reaction fluid and thoroughly washing and/or reconditioning the solid-phase support. Washing typically involves three to seven cycles of adding and removing a wash solvent. Optionally, during the addition steps, multiple building blocks can be added to one reaction vessel in order to synthesize multiple compounds attached to one solid-phase support, or alternatively, the contents of separate reaction vessels can be combined and partitioned in order that multiple compounds can be synthesized in one reaction vessel with each microbead having only one attached final compound (e.g., "split and mix" synthesis). After the desired number of building block addition steps, the final compound is present in the reaction vessel and attached to the solid phase support. The final compounds can be utilized either directly attached to their synthetic solid-phase supports, or alternatively, can be cleaved from their supports. In the latter case, the linker moiety attaching the compound to the solid phase support is cleaved in a variety of ways, and the final compound, or library of compounds is extracted from the reaction vessel into a liquid phase.

In view of the exemplary protocols described herein, an oligonucleotides synthesizer can include facilities for handling fluids, for manipulating reaction vessels, and for storage of reagents and building blocks. In some embodiments, facilities for fluid handling include: facilities to accurately dispense solutions and slurries which contain building blocks, solid-phase substrates, reagents, and/or solvents into the reaction vessels; facilities to rapidly and repetitively add wash solvents into the reaction vessels; and facilities to rapidly and accurately remove fluid phases from the reaction vessels leaving behind the solid-phase supports within the reaction vessels with respective attached intermediate compounds. Facilities for manipulating reaction vessels include: facilities to move reaction vessels; facilities for time and temperature controlled incubation of reaction vessels; and optionally facilities for agitation of reaction vessels during incubation, including without limitation agitation by stirring, tipping, inverting, and the like. Each such protocol uses a plurality of building blocks, one or more activating agents and other reagents, and one or more work solvents. Accordingly, there are storage facilities for the plurality of building blocks solutions, reagents, solvents, etc.

A computer with a system software is utilized to control the valves, pumps, pressure sensor, UV detector inversion, that includes the ability to perform step-wise functions set up in a protocol fashion.

While preferred embodiments of the disclosure are shown and described herein, such embodiments are provided by way of example only and are not intended to otherwise limit the scope of the disclosure. Various alternatives to the described embodiments of the disclosure may be employed in practicing the disclosure.

The following clauses describe certain embodiments.

Clause 1. An oligonucleotide synthesizer comprising a reaction vessel assembly comprising a reaction vessel, wherein the reaction vessel holds an oligonucleotide solid phase synthesis resin and a liquid phase.

Clause 2. The oligonucleotide synthesizer of clause 1, wherein the oligonucleotide solid phase synthesis resin comprises a plurality of discrete resin pieces.

Clause 3. The oligonucleotide synthesizer of clause 1, wherein the plurality of discrete resin pieces comprises a plurality of resin beads.

Clause 4. The oligonucleotide synthesizer of any one of clauses 1 to 3, wherein the reaction vessel assembly further comprises a reaction vessel bracket.

Clause 5. The oligonucleotide synthesizer of clause 4, wherein the reaction vessel bracket is a hinged bracket or a tension bracket.

Clause 6. The oligonucleotide synthesizer of any one of clauses 1 to 5, wherein the reaction vessel assembly further comprises a rotation actuator.

Clause 7. The oligonucleotide synthesizer of clause 6, wherein the reaction vessel assembly further comprises a rotation shaft.

Clause 8. The oligonucleotide synthesizer of any one of clauses 1 to 7, wherein the reaction vessel assembly further comprises an overhead stirring assembly.

Clause 9. The oligonucleotide synthesizer of any one of clauses 1 to 8, wherein the reaction vessel comprises one or more chambers.

Clause 10. The oligonucleotide synthesizer of any one of clauses 1 to 9, wherein the v/v ratio between the plurality of discrete resin pieces and the liquid phase allows for mechanical stirring of the plurality of discrete resin pieces.

Clause 11. A solid phase oligonucleotide synthesis reaction vessel comprising a housing defining a chamber containing a solid phase synthesis resin, and an operable inlet port and an outlet port for fluid communication with said chamber.

Clause 12. The solid phase oligonucleotide synthesis reaction vessel of clause 11, wherein the fluid is gas, liquid, or both.

Clause 13. The solid phase oligonucleotide synthesis reaction vessel of clause 11, wherein the housing is made of glass to allow for visualization of the reaction.

Clause 14. The solid phase oligonucleotide synthesis reaction vessel of any one of clauses 11 to 13, wherein the housing has a volume allowing for the solid phase synthesis resin and for additional volume for resin growth.

Clause 15. The solid phase oligonucleotide synthesis reaction vessel of any one of clauses 11 to 14, further comprising filter plates.

Clause 16. The solid phase oligonucleotide synthesis reaction vessel of clause 15, wherein the filter plates enable filtered fluid flow both in and out of the chamber from the exterior.

Clause 17. The solid phase oligonucleotide synthesis reaction vessel of clause 15, wherein the filter plates maintain the solid phase synthesis resin within the chamber during fluid transfer.

Clause 18. The solid phase oligonucleotide synthesis reaction vessel of any one of clauses 15 to 17, further comprising one or more fixtures for holding the filter plates in place and preventing dislodgement of the filter plates during fluid flow into the chamber.

Clause 19. An oligonucleotide synthesizer comprising the solid phase oligonucleotide synthesis reaction vessel of any one of clauses 11 to 18.

Clause 20. The oligonucleotide synthesizer of clause 19, further comprising a housing and a clamp holding the reaction vessel.

Clause 21. The oligonucleotide synthesizer of clause 19 or clause 20, wherein the inlet and outlet ports for fluid communication are connected to different valve mechanisms and a control system which allows for gas and liquid communication.

Clause 22. The oligonucleotide synthesizer of any one clause 19 or clause 20, whereas the gas communication is connected to a pressure regulator and flow control, to allow for adjustable precision control of gas rate into the housing chamber to bubble the resin within the reaction vessel for mixing.

Clause 23. A solid phase oligonucleotide synthesizer mixer comprising an invertible fixture which holds the reaction vessel, whereas the invertible fixture is connected to a shaft that can axially rotate.

Clause 24. The solid phase oligonucleotide synthesizer mixer of clause 23, wherein the shaft is connected to a pneumatic or electrical actuator, which powers the shaft to axially rotate.

Clause 25. The solid phase oligonucleotide synthesizer mixer of clause 23 or clause 24, wherein the pneumatic or electrical actuator is connected to a control system, which can determine the rate of rotation.

Clause 26. A solid phase oligonucleotide synthesizer mixer comprising a housing defining a chamber containing a solid phase synthesis resin, whereas said housing is made of glass to allow for visualization of the reaction, and contains an multiple operable inlet and outlet port for fluid (both gas and liquid) communication with said chamber.

Clause 27. The solid phase oligonucleotide synthesizer mixer of clause 26, wherein the housing has a port for a stir shaft to enter the chamber, and said port contains a seal around the stir shaft.

Clause 28. The solid phase oligonucleotide synthesizer mixer of clause 26 or clause 27, wherein the stir shaft is connected to a motor which allows for axial rotation of the stir shaft, and the stir shaft within the reaction vessel chamber has one or more agitator blades connected to the stir shaft to allow for mixing of the resin.

Clause 29. The solid phase oligonucleotide synthesizer mixer of any one of clauses 26 to 28, wherein during mixing with said mixers, the operable inlet and outlet port for fluid communication are connected to a pump and in a loop, allowing fluid circulate whereas the fluid path goes out of the outlet port and back into the inlet port.

Clause 30. The solid phase oligonucleotide synthesizer mixer of any one of clauses 26 to 29, wherein during mixing with said mixers, the operable inlet and outlet port for fluid communication are connected to a pump and the inlet port is connected to a solvent reservoir to deliver solvent, and the outlet port is connected to a waste reservoir, and the pump is on allowing for fluid to flow from the solvent reservoir, through the reaction vessel, and to the waste reservoir.

Clause 31. A low cross link resin for a high swelling resin in acetonitrile (ACN) and toluene, wherein the low cross link resin had a higher substitution between 0.3 to 0.8 mmol/g.

Clause 32. The low cross link resin of clause 31, wherein the resin has a pore size between about 300 Å to 1000 Å to facilitate more space for oligo chain growing on resin.

Clause 33. The low cross link resin of clause 31 or clause 32, wherein the cross link resin is in the 1% to 3% level.

Clause 34. The low cross link resin of any one of clauses 31 to 33, wherein the resin can shrink in MeOH to ease the final cleavage.

Clause 35. A process for making an oligonucleotide, comprising reacting a oligonucleotide precursor with a solid phase support, and mechanically stirring the solid phase support.

Clause 36. The process of clause 35, further comprising one or more activation steps.

Clause 37. The process of clause 35 or clause 36, further comprising one or more coupling steps.

Clause 38. The process of any one of clauses 35 to 37, further comprising one or more capping steps.

Clause 39. The process of any one of clauses 35 to 38, further comprising one or more oxidation steps.

Clause 40. The process of any one of clauses 35 to 39, further comprising one or more detritylation steps.

Clause 41. The process of any one of clauses 35 to 40, further comprising one or more cleavage steps.

Clause 42. The process of any one of clauses 35 to 41, further comprising one or more deprotection steps.

Clause 43. The process of any one of clauses 35 to 42, wherein the solid phase support comprises a plurality of discrete resin pieces.

Clause 44. The process of clause 43, wherein the plurality of discrete resin pieces comprises a plurality of resin beads.

Clause 45. The process of any one of clauses 35 to 44, wherein the mechanical stirring of the solid phase support comprises the motion of a reaction vessel comprising the solid support relative to a chassis, frame, or support.

Clause 46. The process of clause 45, wherein the motion comprises one or more of tipping, rocking, shaking, and inverting the reaction vessel relative to the chassis, frame, or support.

Clause 47. The process of any one of clauses 35 to 44, wherein the mechanical stirring of the solid phase support comprises stirring via a stir blade, a stir bar, or both.

Clause 48. The process of any one of clauses 35 to 44, wherein the mechanical stirring of the solid phase support comprises stirring via a plurality of bubbles moving relative to the solid phase support.

A number of patent and non-patent publications are cited herein in order to describe the state of the art to which this disclosure pertains. The entire disclosure of each of these publications is incorporated by reference herein.

While certain embodiments of the present disclosure have been described and/or exemplified above, various other embodiments will be apparent to those skilled in the art from the foregoing disclosure. The present disclosure is, therefore, not limited to the particular embodiments described and/or exemplified, but is capable of considerable variation and modification without departure from the scope and spirit of the appended claims.

The invention claimed is:

1. A process for making an oligonucleotide, comprising:
reacting a oligonucleotide precursor with a solid phase support within a reaction vessel, the reaction vessel being coupled to an actuator and having a resting position; and
inverting the reaction vessel via the actuator such that the reaction vessel is inverted relative to the resting position, wherein the inversion of the reaction vessel results in stirring of the solid phase support within the reaction vessel,
wherein the reaction vessel includes a first chamber in fluid communication with a second chamber via a connecting passage, wherein the connecting passage has a width less than a width of the first chamber and the second chamber.

2. The process of claim 1, further comprising one or more of: activation of one or more agents and/or reagents, coupling via delivery of an amidite to the reaction vessel, capping via one or more reagents, oxidation, detritylation, cleavage, and deprotection.

3. The process of claim 1, wherein the solid phase support comprises a plurality of discrete resin pieces.

4. The process of claim 3, wherein the plurality of discrete resin pieces comprises a plurality of resin beads.

5. The process of claim 1, wherein the inverting of the reaction vessel includes inversion of the reaction vessel by the actuator relative to a chassis, frame, or support.

6. The process of claim 5 further comprising one or more of tipping, rocking, and shaking the reaction vessel relative to the chassis, frame, or support.

7. The process of claim 1, wherein the reaction vessel includes a stir blade, a stir bar, or both, the stir blade and the stir bar configured to agitate the solid phase support.

8. The process of claim 1, wherein the reaction vessel includes a plurality of bubbles, the plurality of bubbles configured to move relative to the solid phase support and agitate the solid phase support.

9. The process of claim 3, wherein the plurality of discrete resin pieces comprise a low cross link resin, wherein the low cross link resin has a higher substitution between 0.3 to 0.8 mmol/g and the low cross link resin is configured for high swelling in acetonitrile.

10. The process of claim 9, wherein the low cross link resin has a pore size between about 300 Å to 1000 Å.

11. The process of claim 1, wherein the reaction vessel is coupled to the actuator via a bracket, the bracket having a connecting feature to couple the bracket to the actuator.

12. The process of claim 11, wherein the connecting feature of the bracket is coupled to the actuator by a shaft, the shaft configured to transfer movement of the actuator to the bracket and the reaction vessel.

13. The process of claim 11, wherein the bracket includes a retaining feature configured to secure the reaction vessel to the bracket.

14. The process of claim 1, wherein the inverting of the reaction vessel includes deviating the reaction vessel from the resting position by a predetermined angle.

15. The process of claim 14 further comprising calculating the predetermined angle using an electronic device coupled to the actuator.

16. The process of claim 1, wherein the reaction vessel is inverted relative to the actuator.

* * * * *